(12) United States Patent
Bouttens et al.

(10) Patent No.: US 8,361,157 B2
(45) Date of Patent: *Jan. 29, 2013

(54) METHOD OF IMPLANTING A SHOULDER PROSTHESIS ASSEMBLY

(75) Inventors: Denis Bouttens, Le Touquet (FR); Michel De Buttet, Croix (FR); Didier Capon, Sautron (FR); Michel Colmar, Saint Brieuc (FR); Cecile Nerot, Reims (FR); Philippe Valenti, Champigny sur Marne (FR); Hassan Wahab, Angers (FR)

(73) Assignee: Depuy France, Saint-Priest (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/574,808

(22) Filed: Oct. 7, 2009

(65) Prior Publication Data

US 2010/0023068 A1  Jan. 28, 2010

Related U.S. Application Data

(63) Continuation of application No. 11/183,826, filed on Jul. 19, 2005, now Pat. No. 7,611,539, which is a continuation of application No. 10/168,802, filed as application No. PCT/FR00/03539 on Dec. 14, 2000, now Pat. No. 6,953,478.

(30) Foreign Application Priority Data

Dec. 23, 1999 (FR) ...................................... 99 16420

(51) Int. Cl.
A61F 2/40 (2006.01)
(52) U.S. Cl. .................................................... 623/19.11
(58) Field of Classification Search .... 623/19.11–19.14, 623/20.11–20.13, 21.11–21.19; 606/90, 606/99, 86 R; A61F 2/40
See application file for complete search history.

(56) References Cited

U.S. PATENT DOCUMENTS

| 3,815,157 | A | | 6/1974 | Skorecki et al. |
| 3,869,730 | A | | 3/1975 | Skobel |
| 3,916,451 | A | | 11/1975 | Buechel et al. |
| 3,978,528 | A | | 9/1976 | Crep |
| 4,040,131 | A | | 8/1977 | Gristina |
| 4,530,114 | A | * | 7/1985 | Tepic .......................... 623/23.11 |
| 4,693,723 | A | | 9/1987 | Gabard |
| 4,964,865 | A | | 10/1990 | Burkhead et al. |
| 5,181,928 | A | | 1/1993 | Bolesky et al. |

(Continued)

FOREIGN PATENT DOCUMENTS

| EP | 0 058 744 | 9/1982 |
| EP | 0 243 298 | 10/1987 |

(Continued)

OTHER PUBLICATIONS

Delta 3.1—applicants internal memo comparing two versions of the device, labeled "V1: Oct. 1996".

(Continued)

*Primary Examiner* — Thomas J Sweet
*Assistant Examiner* — Cheryl Miller
(74) *Attorney, Agent, or Firm* — Young & Thompson

(57) ABSTRACT

A shoulder prosthesis assembly includes a metaglenoid element (7) having a plate (13) with a central tubular bushing (14) and members for anchoring it in the glenoid cavity. The assembly also includes a glenoid sphere (9) that fits over the metaglenoid element which has an axial screw that is (35) screwed into the bushing. The glenoid sphere has a member to facilitate installation thereof on the metaglenoid element. The member may include a pin (46) adapted to slide in the tubular bushing (14) and in an axial channel of the screw, so that the glenoid sphere (9) can be screwed into place without any risk of damaging the thread of the screw or the tapping of the bushing.

18 Claims, 4 Drawing Sheets

U.S. PATENT DOCUMENTS

| | | | |
|---|---|---|---|
| 5,314,479 A | 5/1994 | Rockwood et al. | |
| 5,462,563 A | 10/1995 | Shearer et al. | |
| 5,725,595 A | 3/1998 | Gustilo | |
| 6,136,032 A | 10/2000 | Viladot Perice et al. | |
| 6,197,063 B1 | 3/2001 | Dews | |
| 6,228,120 B1 * | 5/2001 | Leonard et al. | 623/19.12 |
| 6,283,999 B1 | 9/2001 | Rockwood, Jr. | |
| 6,474,918 B1 | 11/2002 | Kelch | |
| 6,953,478 B2 | 10/2005 | Bouttens et al. | |
| 6,969,406 B2 | 11/2005 | Tornier | |
| 7,611,539 B2 * | 11/2009 | Bouttens et al. | 623/19.11 |
| 2003/0149485 A1 | 8/2003 | Tornier | |
| 2003/0158605 A1 | 8/2003 | Tornier | |

FOREIGN PATENT DOCUMENTS

| | | |
|---|---|---|
| EP | 0 379 785 | 8/1990 |
| EP | 0 552 950 | 7/1993 |
| EP | 0 581 667 | 2/1994 |
| EP | 0 634 154 | 1/1995 |
| EP | 0 815 808 | 1/1998 |
| EP | 0 884 032 | 12/1998 |
| EP | 0 910 999 | 4/1999 |
| EP | 1 332 734 | 8/2003 |
| FR | 2 605 514 | 4/1988 |
| FR | 2 618 065 | 1/1989 |
| FR | 2 652 498 | 4/1991 |
| FR | 2704747 | 6/1993 |
| FR | 2 689 756 | 10/1993 |
| FR | 2 699 400 | 6/1994 |
| FR | 2 704 747 | 11/1994 |
| FR | 2 737 107 | 1/1997 |
| GB | 2 375 052 | 3/2004 |
| WO | 01/47442 | 7/2001 |

OTHER PUBLICATIONS

Internal memo describing applicant's device (Delta 3.1).

* cited by examiner

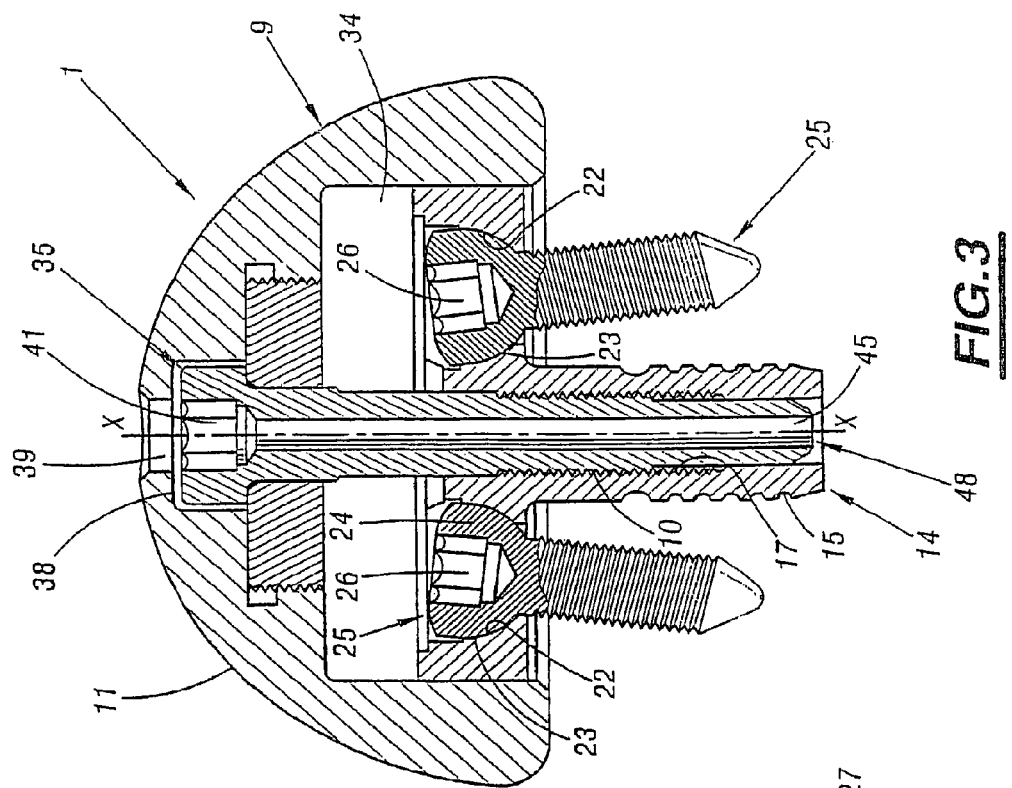
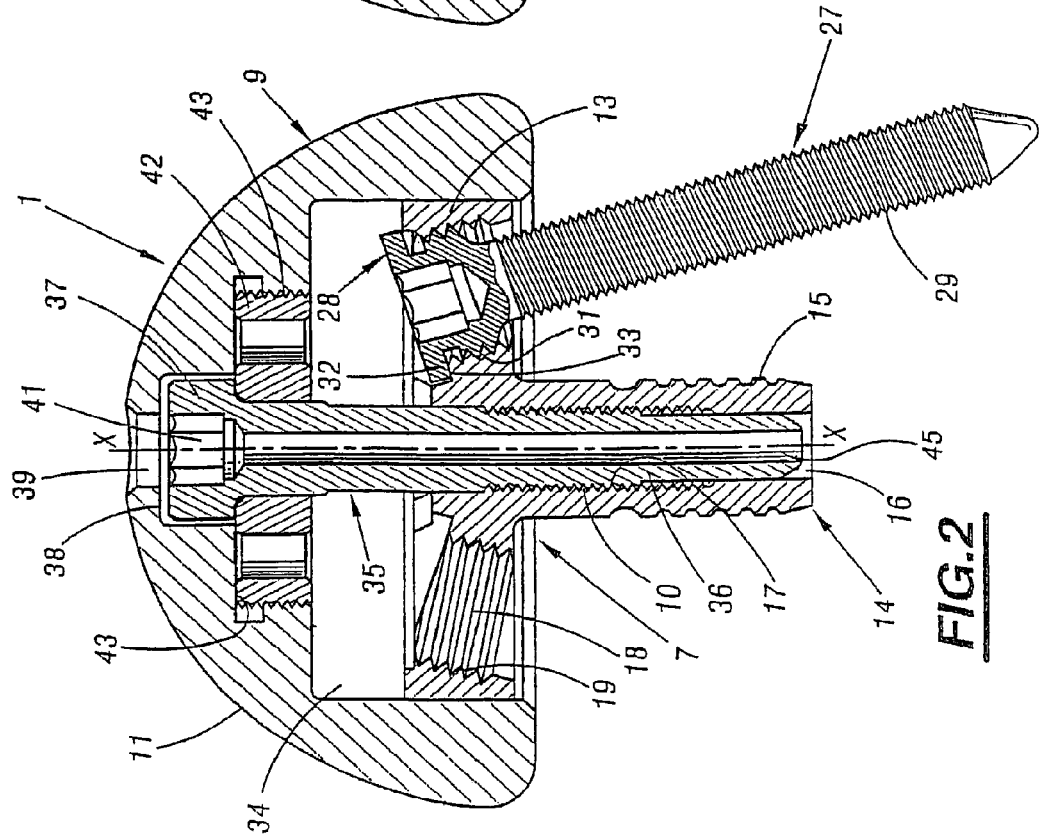

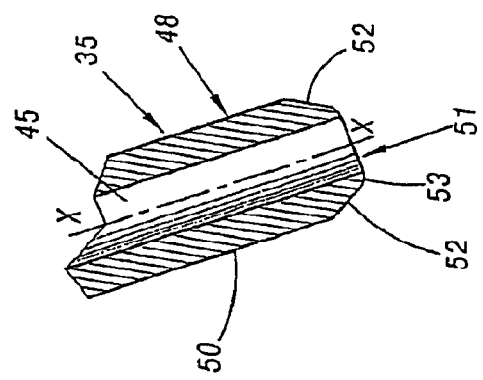
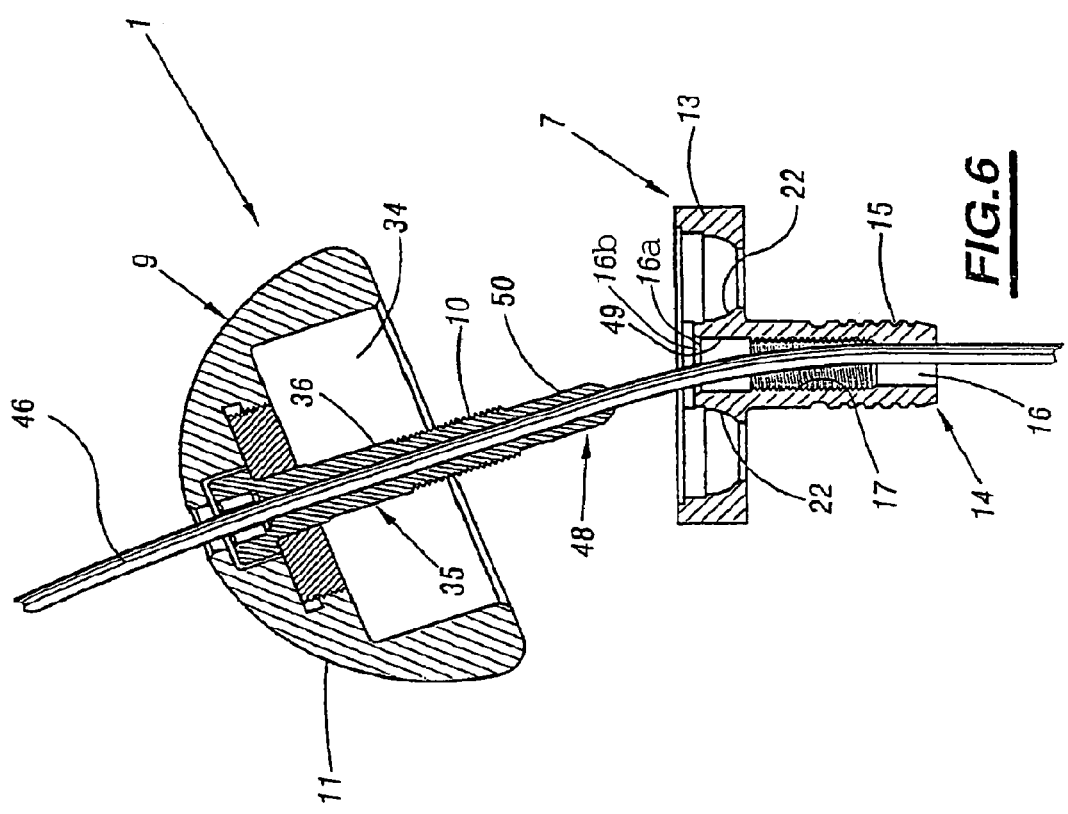

METHOD OF IMPLANTING A SHOULDER PROSTHESIS ASSEMBLY

CROSS REFERENCE TO RELATED APPLICATIONS

This application is a continuation of Application No. 11/183,826 filed on Jul. 19, 2005, now U.S. Pat. No. 7,611,539, which is a continuation of 10/168,802, filed on Oct. 30, 2002, now U.S. Pat. No. 6,953,478, which is a National Stage of PCT/FR00/03539 filed on Dec. 14, 2000, which claimed priority to French Application No. 9916420 filed Dec. 23, 1999. The entire contents of each of the above-identified applications are hereby incorporated by reference.

BACKGROUND OF THE INVENTION

The present invention relates to a shoulder prosthesis assembly of the type comprising a metaglenoid element formed by a plate provided with a central tubular bushing together with members for anchoring in the glenoid cavity, and a glenoid sphere adapted to be fitted over the metaglenoid element. The glenoid sphere is provided with an axial screw that is free to turn relative to the glenoid sphere. This screw is adapted to be screwed into the bushing of the metaglenoid element. The glenoid sphere has a convex joint surface for co-operating with a concave cup of an associated humeral prosthesis.

The invention also provides a prosthesis forming part of the prosthesis assembly.

A prosthesis of this type is known, for example, from French patent No. 89/13366 (2 652 498) filed in the name of Medinov.

It is known that the rotator cuff is constituted by the set of shoulder muscles which comprise the deltoid, the supraspinatus, the infraspinatus, the infrascapular, and the smaller round. When massive rupture occurs of the cuff, only the deltoid remains, and that is insufficient for enabling the shoulder joint to operate properly, which requires a shoulder prosthesis to be implanted.

Prostheses are known in which the metaglenoid element is fastened to the glenoid cavity of the scapula by a plurality of screws and receives a glenoid sphere having a convex joint surface, which sphere is screwed to the periphery of the metaglenoid element.

Unfortunately, it is found that after being in use for a certain length of time, the glenoid sphere tends to become unscrewed. This causes the glenoid sphere to tilt under the metaglenoid element and destroys the threads . . . . This damage caused to the prosthesis can be sufficient to require a surgeon to remove the entire prosthesis in order to replace it.

To solve this problem, proposals were initially made to cause the facing contacting surfaces of the glenoid sphere and the metaglenoid element to be rough. That technique has turned out to be insufficient.

Proposals were then made to associate the screw of the glenoid sphere with an arrangement of complementary male and female conical bearing surfaces made respectively on the metaglenoid element and the glenoid sphere. The two conical bearing surfaces can then be moved apart or towards each other as a function of the direction in which the screw is driven in order to lock or unlock the system comprising the glenoid sphere and the metaglenoid element. A shoulder prosthesis arranged in that way is described in French patent No. 95/09395 (2 737 107) in the name of Medinov. That prosthesis gives satisfaction.

However, the heads of the screws can pass right through the metaglenoid element at the end of screw tightening if the surgeon cannot feel this end appropriately, since no special retaining means are provided. Under such circumstances, the metaglenoid element is no longer fixed to the glenoid cavity.

Another problem lies in giving the surgeon access to the metaglenoid element, which raises a difficulty with putting the glenoid sphere properly into place on the metaglenoid element. The patient is in a semi-seated position during surgery, such that the surgeon has to approach the metaglenoid element from a cantilevered-out position, with the metaglenoid element being, as it were, at the bottom of a well defined by the tissues and the muscles of the shoulder. Access to the metaglenoid element is narrow and relatively difficult, with poor visibility that makes it impossible to tell whether the glenoid sphere screw is exactly on the axis of the metaglenoid bushing.

It results that the surgeon can position the glenoid sphere incorrectly, so that the axial screw of the glenoid sphere is not exactly on the axis of the corresponding hole in the metaglenoid element. Under such circumstances, screw tightening is started when the thread on the glenoid sphere screw and the tapping in the central hole of the metaglenoid element are not properly engaged. Once the surgeon becomes aware of this faulty insertion, the threads have already become sufficiently damaged to require the entire prosthesis to be replaced. Not only must two prostheses be used, thus considerably increasing equipment cost, but the time required for the operation is doubled.

SUMMARY OF THE INVENTION

The object of the invention is to provide a glenoid prosthesis that is arranged in such a manner as to eliminate those various drawbacks.

According to the invention, the shoulder prosthesis includes means for guiding the glenoid sphere and adapted to facilitate proper placement of the screw on the metaglenoid element on the axis of the bushing.

In an embodiment of the invention, said guide means comprise a pin adapted to be capable of being slid in the tubular bushing, and the screw of the glenoid sphere presents a longitudinal axial channel opening out to both ends of the screw and allowing the pin to be inserted into said channel, such that the pin serves to guide the glenoid sphere when the screw slides along the pin until it is inserted into the tubular bushing.

Preliminary insertion of the pin in the central bushing of the metaglenoid element makes it possible to provide complete guidance of the glenoid sphere onto the axis of the central bushing of the metaglenoid element. The glenoid sphere screw can then be screwed properly into the metaglenoid bushing without any risk of damaging the threads, thereby almost completely eliminating any risk of needing to have recourse to a second prosthesis.

According to another characteristic of the invention, the members for anchoring the metaglenoid element in the glenoid cavity are screws, and means are provided to ensure that each screw comes into abutment against the metaglenoid element at the end of screw tightening.

In an embodiment of the invention, the abutment means comprise a collar formed around the head of at least one screw and projecting radially relative to a thread of the screw head, and a corresponding annular bearing shoulder arranged around the edge of a tapped hole for insertion of the screw in the metaglenoid element.

According to another possible characteristic of the invention, the abutment means comprise at least one head of a screw presenting a convex outside surface adapted to bear against a complementary concave seat formed in the wall of a hole for inserting said screw in the metaglenoid element.

These arrangements thus avoid any risk of the screw passing through the metaglenoid element at the end of screw tightening, thus guaranteeing security in the fixing of the metaglenoid element to the glenoid cavity.

BRIEF DESCRIPTION OF THE DRAWINGS

Other features and advantages of the invention appear from the following description given with reference to the accompanying drawings which show an embodiment by way of non-limiting example.

FIG. 2 is a view on a larger scale, showing the glenoid prosthesis of FIG. 1 in axial section on 2/2 of FIG. 4.

FIG. 3 is a view of the glenoid prosthesis in section on 3/3 of FIG. 4.

FIG. 6 is a view analogous to FIG. 5 showing the operation of engaging the glenoid sphere on the metaglenoid element by means of a guide pin.

FIG. 7 is a fragmentary axial section view on a larger scale than FIG. 5 showing the free end of the axial screw of the glenoid sphere.

DETAILED DESCRIPTION OF THE PREFERRED EMBODIMENTS

Figure 1:
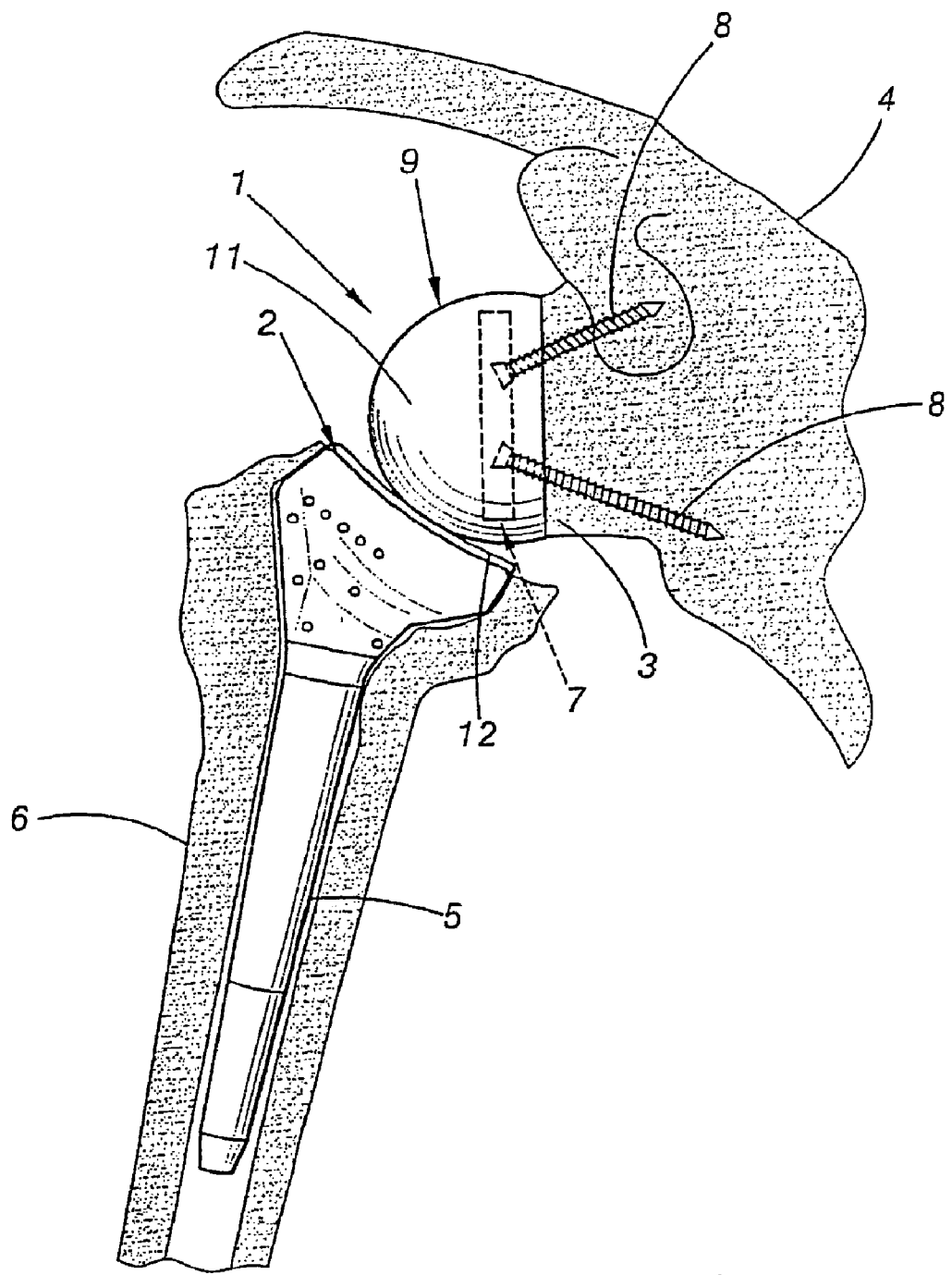
FIG. 1 is an elevation view in a front plane and on a small scale of a total shoulder prosthesis including a glenoid implant in accordance with the invention.

The total shoulder prosthesis shown in FIG. 1 comprises a glenoid implant 1 and a humeral implant 2, respectively secured to the glenoid cavity 3 of a scapula 4 and in the medullar canal 5 of a humerus 6.

The glenoid implant 1 comprises both a metaglenoid element 7 formed by a plate 13 (FIGS. 2 to 6) provided with a plurality of screws 8 for anchoring it in the glenoid cavity 3, two of which screws can be seen in FIG. 1, and also a glenoid sphere 9 adapted to be fitted over the metaglenoid element 7.

The glenoid sphere 9 presents a joint surface 11 which is convex in this embodiment, for co-operating with a complementary surface of a cup 12 of the associated humeral prosthesis 2. In this embodiment, the cup 12 has a concave surface complementary to the convex surface 11.

Figure 5:
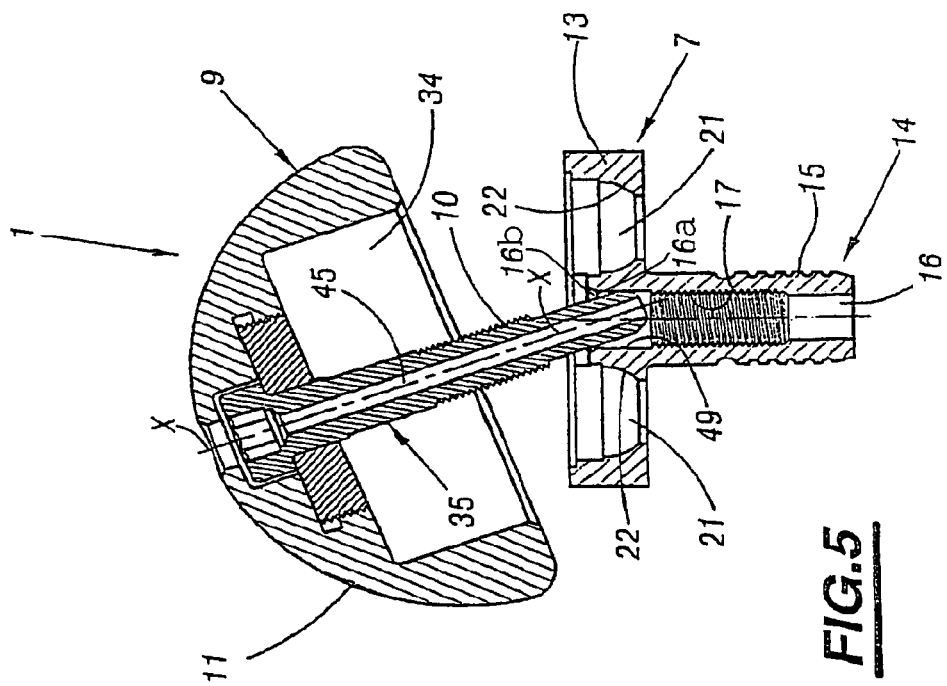
FIG. 5 is a view of the shoulder prosthesis in axial section on 3/3 of FIG. 4, showing the beginning of the operation of inserting the axial screw of the glenoid sphere into the central bushing of the metaglenoid element.
Figure 4:
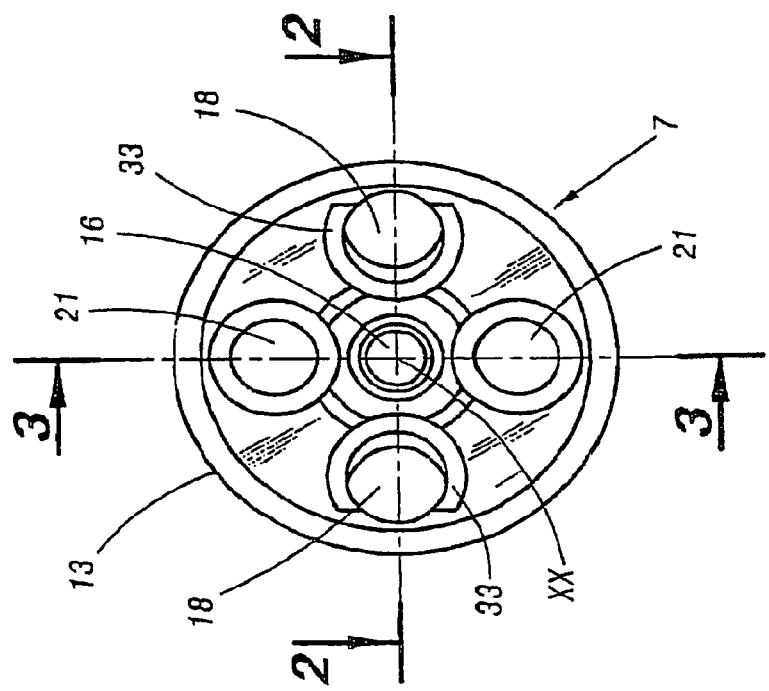
FIG. 4 is a plan view of the metaglenoid element of the shoulder prosthesis of FIGS. 1 to 3.

The plate 13 is preferably conical, being circularly symmetrical about an axis X-X and being fitted with a central tubular adapter or bushing 14 that is preferably integrally formed with the plate 13. The central bushing 14 projects from the plate 13 and has circular ribs 15 to anchor in the bone of the metaglenoid element 7. The bushing 14 presents an axial bore 16 that has tapping 17 over a fraction of its length. The tapping 17 is extended by a bore 49 constituting a smooth zone. An opening 16a communicates with the bore 16 and a countersink 16b communicates with the opening 16a and the bore 16, as seen in FIGS. 5 and 6.

The plate 13 is pierced by four holes for passing the glenoid anchor screws of the metaglenoid element 7. Two of these holes 18 are diametrically opposite and present tapping 19. Their axes diverge symmetrically about the axis X-X. The other two holes 21 are diametrically opposite and are offset from the holes 18 by angular intervals that are preferably equal to 90°. The non-tapped holes 21 are defined by walls 22 constituting concave bearing seats for complementary convex surfaces 23 defining the heads 24 of the bone-anchor screws 25 for anchoring the metaglenoid element 7 in the glenoid cavity 3 (FIG. 3).

The seats 22 are oriented in such a manner that once the screws 25 have been put into place thereon they are disposed so as to diverge relative to the central bushing 14 and symmetrically thereabout. Sockets 26, e.g. hexagonal sockets, are formed in the heads 24 to enable the screws 25 to be tightened by means of a corresponding tool (not shown).

The holes 18 can receive diverging screws 27 each constituted by a head 28 and a threaded shank 29. The head 28 has a thread 31 suitable for screwing into the tapping 19, and an end collar 32 formed around the head 28. The collar 32 projects radially relative to the tapping 31 and can be brought to bear against a corresponding angular shoulder 33 arranged around the edge of the hole 18 in which the screw 27 is inserted.

The collar 32 constitutes abutment means for the screw 27 in the glenoid cavity 3 at the end of screw tightening, preventing the screw 27 from being moved in further as soon as the collar 32 comes into abutment on the associated shoulder 33. Similarly, the concave seats 22 act relative to the associated screws 25 as abutments for stopping them in the metaglenoid element 7 once they have been screwed into the glenoid cavity 3, as soon as the screws 25 have been engaged far enough for the surfaces 23 of the heads 24 to come into contact with the seats 22.

This arrangement prevents the screws 25 and 27 from passing through the metaglenoid element 7 at the end of screw tightening.

The glenoid sphere 9 is made of a substantially hemispherical part whose spherical surface 11 is complementary to the corresponding joint surface of the cup 12. The glenoid sphere 9 has arranged therein a conical recess 34 that is circularly symmetrical about the axis X-X, and that is dimensioned in such a manner as to enable the plate 13 to be inserted therein. The glenoid sphere, which is circularly symmetrical about the axis X-X, is then fitted over the metaglenoid element 7.

The glenoid sphere 9 is provided with an axial screw 35 that is free to rotate relative to the glenoid sphere 9. The shank 36 of the screw 35 presents a thread 10 over a fraction of its length and it can be screwed into the tapping 17 of the bushing 14. The screw 35 has a head 37 suitable for being inserted in a housing 38 that is circularly symmetrical about the axis X-X and that opens out into the polar cap of the surface 11 via an axial orifice 39. This orifice allows the end of a tool for tightening the screw 35 to be inserted, which tool can be received in a socket 41 of complementary shape.

After the head 37 has been inserted in the housing 38, the screw 35 is held in place by a threaded washer 42 placed in a tapped housing 43 that is coaxial with the housing 38 about the axis X-X.

A longitudinal axial channel 45 is arranged in the screw 35 opening out at both ends of the screw, i.e. at one end in the socket 41 and in the orifice 39. The prosthesis assembly also comprises means for guiding the glenoid sphere 9, and adapted to make it easier to install on the metaglenoid element 7. In the embodiment shown, these guide means comprise a pin 46 that preferably presents some flexibility, being adapted to be slid initially into the axial bore 16 of the bushing 14 and secondly through the longitudinal channel 45 of the screw 35 (FIG. 6). The pin 46 is preferably made of metal, and its diameter is advantageously slightly smaller than the diameter of the channel 45 in the screws 35.

The screw 35 has a smooth free end 48 whose tip is chamfered so as to facilitate insertion into the inlet of the tubular bushing 14. The guide means for the screw 35 further comprise the bore constituting a smooth cylindrical zone 49 arranged in the inlet of the bushing 14 and followed by the tapping 17. The chamfered tip 51 preferably has an annular surface 52 whose longitudinal section is rectilinear (i.e. a conical surface) and which is followed to the free end of the tip 51 by a rounded annular surface 53, preferably constituted by a spherical fillet. At its end remote therefrom, the conical section 52 joins a smooth zone 50 followed by the thread 10.

The pin 46 is used by the surgeon as follows.

The metaglenoid element 7 is initially anchored in the glenoid cavity 3 by impacting the bushing 14 and by tightening the screws 25, 27. Thereafter, the surgeon inserts one end of the pin 46 in the bore 16 of the bushing 14. Using a screwdriver that has a cannula, the surgeon then presents the glenoid sphere 9 to the inlet of the well formed in the tissues and the muscles of the shoulder, with the bottom of the well being constituted by the metaglenoid element 7, the end of the pin 46 being threaded into the axial channel 45. The surgeon then causes the glenoid sphere 9 to slide along the pin 46 until the free end 48 of the screw 35 engages in the bore constituting a smooth zone 49 (FIG. 6). The chamfered and rounded tip 51 makes it easier to insert the screw 35 into the bushing 14 without damaging the tapping 17 because of the bore constituting a smooth zone 49, and without damaging the thread 10 because of the smooth zone 50. As soon as the screw 35 is properly on the axis X-X of the bushing 14, the surgeon tightens the screw 35 until the glenoid sphere 9 becomes impacted on the metaglenoid element 7 (FIGS. 3 and 4) and then withdraws the screwdriver and the pin.

The arrangement of the rounded fillet 53 of the conical zone 52, of the smooth zone 50, and of the bore constituting a smooth zone 49 of the bushing 14 can be arranged to provide proper guidance for the screw 35 in the bushing 14, either in combination with a guide pin 46 (FIGS. 5 and 6) or without one. Under such circumstances, the screw 35 can have the axial channel 45 or it can be solid. Nevertheless, the combination of the bore 16, the pin 46, the end 48 with its smooth zone 50, and the bore constituting a smooth zone 49 of the bushing 14 provides the most satisfactory guidance for the glenoid sphere 9 up to its proper position on the axis X-X of the metaglenoid element 7.

In other words, the following variants are possible:
the screw 35 can have a cannula, i.e. can present the axial channel 45 and can be used together with the guide pin 46 without any offset between the thread of the screw 35 and the tapping of the bushing 14: under such circumstances, the thread 10 extends almost to the free end of the screw 35, and the bore constituting a smooth zone 49 is replaced by additional tapping 17;
the screw 35 does not have a cannula, and therefore does not present an axial channel 45, but the thread 10 and the tapping 17 are offset as shown in the drawings, i.e. a smooth zone 50 is provided on the screw 35 and a bore constituting a smooth inlet zone 49 is arranged in the bushing 14; and
the screw 35 has a cannula and in addition the thread 10 and the tapping 17 are offset, i.e. the smooth zone 50 and the tip 51 are arranged on the end 48 of the screw, while a bore constituting a smooth zone 49 is arranged in the inlet of the bore 16 in the bushing 14.

The end 48 of the screw 35 can have a different profile, for example it could have a simple conical chamfer such as 52, or it could have no more than a rounded end fillet of appropriate size.

The indications for the above-described glenoid prosthesis 1 are essentially as follows: traumatisms, arthrosis between the humerus and the scapula, rheumatoid polyarthritis. In general, the shoulder prosthesis of the invention is indicated for pathologies of the rotator cuff.

The invention claimed is:

1. A method of implanting a shoulder prosthesis assembly in a glenoid cavity, comprising the steps of:
providing
(i) a metaglenoid element having a plate fitted with a central adapter, the central adapter including a central axial bore, the axial bore having both (a) a smooth zone at one end thereof and (b) a threaded zone adjacent said smooth zone,
(ii) a glenoid sphere having a recess formed therein, and a joint surface for co-operating with a cup of an associated humeral prosthesis, and
(iii) an axial screw disposed within the recess and rotatable relative to the glenoid sphere, the axial screw including a head at one end thereof, a threaded portion at an intermediate portion thereof, and a smooth surface at an opposing distal insertion end thereof, said smooth surface extending over a fraction of a length of the axial screw, anchoring the metaglenoid element in the glenoid cavity;
inserting the distal insertion end of the axial screw into the axial bore so that the smooth surface contacts the smooth zone of the axial bore; and
positioning the plate within the recess.

2. The method according to claim 1, further comprising the step of aligning an axis of the axial screw with an axis of the central axial bore.

3. The method according to claim 2, further comprising the step of rotating the axial screw relative to the plate until the plate is impacted against an inner surface of the recess.

4. The method according to claim 3, wherein the axial screw is rotatably connected to the glenoid sphere.

5. The method according to claim 1, further comprising inserting a pin into a longitudinal axial channel of the axial screw, and guiding the glenoid sphere as the axial screw slides along the pin during the inserting of the distal insertion end of the axial screw into the central axial bore.

6. The method according to claim 1, further comprising rotating the axial screw relative to the plate until the plate impacts against an inner surface of the recess.

7. The method according to claim 1, further comprising tightening at least one anchoring member to abut the at least one anchoring member against abutment elements of the metaglenoid element.

8. The method according to claim 7, wherein the abutment elements include a collar formed around a head of the at least one anchoring member and projecting radially relative to a thread of the at least one anchoring member, and a corresponding annular bearing shoulder arranged around an edge of a threaded hole for insertion of the at least one anchoring member in the metaglenoid element.

9. The method according to claim 7, wherein the abutment elements include a concave seat formed in a wall of a hole in the plate for inserting the at least one anchoring member in the metaglenoid element, and wherein a head of the at least one anchoring member presents a convex outside surface adapted to bear against a concave seat.

10. The method according to claim 1, wherein the plate includes a plurality of equidistance spaced holes.

11. The method according to claim 10, further comprising inserting a corresponding screw into the metaglenoid element such that a head of the corresponding screw presents a convex outside surface adapted to bear against a concave seat formed in a wall of a respective one of the holes.

12. The method according to claim 10, wherein the plurality of holes consists of four holes.

13. The method according to claim 12, wherein the four holes comprise two opposing threaded holes and two opposing unthreaded holes.

14. The method according to claim 13, further comprising inserting first and second screws into the metaglenoid element such that a head of one of said first and second screws presents a convex outside surface to bear against a concave seat formed in a respective wall of said unthreaded holes.

15. The method according to claim 1, wherein an entire length of the axial screw is cannulated.

16. The method according to claim 1, wherein the metaglenoid element is secured to the glenoid cavity of a scapula.

17. A method of implanting a shoulder prosthesis assembly in a glenoid cavity, comprising the steps of:

using a glenoid implant (1) comprising both (i) a metaglenoid element (7) formed of a plate (13) provided with a plurality of screws for anchoring the plate, and (ii) a glenoid sphere (9) adapted to be fitted over the metaglenoid element (7), the glenoid sphere (9) having a housing (38) presenting an exterior joint surface (11) shaped for co-operating with a complementary surface of a humeral implant (2), the housing (38) circularly symmetrical about an axis (X-X) and having an opening into a polar cap of the exterior joint surface (11) via an axial orifice (39), the plate (13) being fitted with a central tubular adapter (14), the tubular adapter (14) projecting from the plate (13) and having ribs (15) on an exterior surface thereof, the tubular adapter (14) presenting an axial bore (16) with a tapping (17) over a fraction of the axial bore's length and an adjacent smooth zone (49) extending to an exterior surface opening (16a) of the plate (13), the plate (13) comprising four holes for passing the screws of the metaglenoid element (7), a first two opposing holes (18) of the four holes comprising another tapping (19), axes of said first two opposing holes (18) diverging symmetrically about said axis (X-X), a second two opposing holes (21) of the four holes being offset from the first two holes (18) and being non-tapped holes, the glenoid sphere (9) having a recess (34) circularly symmetrical about said axis (X-X), the recess (34) dimensioned to enable the plate (13) to be inserted therein, the glenoid sphere (9) provided with an axial screw (35) free to rotate relative to the glenoid sphere (9) and connected to the glenoid sphere (9), a shank (36) of the axial screw (35) presenting i) a thread (10) over an intermediate fraction of a length thereof allowing the shank (36) to be screwed into the tapping (17) of the tubular adapter (14), ii) a head (37) inserted in the housing (38) via the axial orifice (39) with the axial screw head (37) exposed through the exterior joint surface (11) of the glenoid sphere (9), and iii) a smooth surface extending over a distal insertion end of the shank opposite the head (37), anchoring the metaglenoid element in the glenoid cavity;

inserting the distal insertion end of the axial screw into the axial bore so that the smooth surface contacts the smooth zone of the axial bore; and positioning the housing about the plate.

18. The method according to claim 1, wherein a washer rotatably connects the axial screw to the glenoid sphere, the washer defining an abutment surface for abutment of the head of the axial screw and thereby holding the axial screw in place, the washer having a passage allowing free rotation of the axial screw relative to the glenoid sphere, the plate and the central adapter of the metaglenoid element being distinct from the washer.

* * * * *